United States Patent [19]
Ballagh et al.

[11] Patent Number: 5,486,360
[45] Date of Patent: Jan. 23, 1996

[54] METHOD OF TREATING TUMOUR CELLS USING CATALASE

[75] Inventors: Robert H. Ballagh, 125 Bell Farm Rd. Suite 203, Barrie, Ontario, Canada, L4M 6L2; Jeff B. Jones, 217 Pembroke Street East, Pembroke, Ontario, Canada, K8A 3J8

[73] Assignees: St. Joseph Health Centre; The Lawson Research Institute, both of London; Robert H. Ballagh, Barrie; Jeff B. Jones, Pembroke, all of Canada

[21] Appl. No.: 50,776

[22] Filed: Apr. 22, 1993

[51] Int. Cl.$^6$ ................................................. A61K 38/44
[52] U.S. Cl. ........................................................ 424/94.4
[58] Field of Search ................................ 424/94.1, 94.2, 424/94.4, 94.5

[56] References Cited

U.S. PATENT DOCUMENTS

| | | | |
|---|---|---|---|
| 4,282,232 | 8/1981 | Agrawal | 514/326 |
| 4,346,174 | 8/1982 | Yasuda | 435/189 |
| 4,462,992 | 7/1984 | Agrawal et al. | 514/43 |
| 4,599,234 | 7/1986 | Amer | 424/164 |
| 4,681,756 | 7/1987 | Mereens et al. | 424/451 |
| 5,001,141 | 3/1991 | Kerr et al. | 514/398 |
| 5,009,891 | 4/1991 | Niwa et al. | 424/195.1 |
| 5,036,096 | 7/1991 | Suto | 514/398 |
| 5,073,639 | 12/1991 | Suto | 548/327.5 |
| 5,091,180 | 2/1992 | Walker et al. | 424/94.4 |
| 5,143,836 | 9/1992 | Hartman et al. | 435/189 |
| 5,171,680 | 12/1992 | Mullenbach et al. | 435/189 |

FOREIGN PATENT DOCUMENTS

| | | |
|---|---|---|
| 2038577 | of 0000 | Canada . |
| 2052713 | of 0000 | Canada . |
| 0032422 | 4/1981 | Japan ................ 424/94.4 |

OTHER PUBLICATIONS

Grosch, D. S., Hopwood, L. E., Biological Effects of Radiations, Academic Press, New York, San Francisco, pp. 175–210, 1979.
Peters, L. J., Thawley, S. E., Panje, W. R., ed. Comprehensive Management of Head and Neck Tumours, W. B. Saunders Philadelphia, London, Toronto, pp. 132–152, 1987.
Petkau, A., et al. Life Sci. 22:867–882, 1978.
Clark I. A., Pathology, 18:181–186, 1986.
Thomas, J. K. Silini, G. ed. Radiation Research 179–194, 1966.
Southorn, P. A., Mayo Clin Proc. 63:381–389 (1988).
Grezlinska, E. et al, Int. J. Radiat. Biol. 41:473–481, 1982.
McLennan G., Autor, A. P., Autor, A. P. ed. Pathology of Oxygen, Academic Press, New York, pp. 85–97, 1982.
Petkau, A., Br. J. Cancer 55: Suppl VIII, 87–95, 1987.
Misra, H. P. and Fridovich, I., Arch. Biochem. Biophys. 176:577–581, 1986.
Schor, N. F., Biochem. Pharmacol. 37(9):1751–1762, 1988.
Fridovich, I., Autor, A. P. ed Pathology of Oxygen Academic Press, New York, pp. 1–20 1982.
McCord, J. M., J. Free Radio. Biol. Med. 2:307–310, 1986.
McCord J. M., Science 185:529–531, 1974.
McCord, J. M. et al, Autor, A. P. ed Pathology of Oxygen: Academic Press, New York, pp. 75–83, 1982.
Petrone, W. F. et al, Proc. Natl. Acad. Sci. USA, 77:1159–1163, 1980.
Autor, A. P. Life Science, 14:1309–1319, 1974.
McCord, J. M., Fed. Proc., 46:2402–2406, 1987.
Koyama, J. et al, Transplantation, 40:590–595, 1985.
Atalla, SI. et al, Transplantation, 40:584–590, 1985.
Manson, P. N. et al, Ann. Surg. 198:87–90, 1983.
Petkau, A. et al, Biochem. Biophys. Res. Commun., 67:1167–1174, 1975.
Edsmyr, F., Autor, A. P. ed Pathology of Oxygen, Academic Press, New York, pp. 315–326, 1982.
Westman, N. G. and Marklund, S. L., Acta Oncologica, 26:483–487, 1987.
Scott, M. D. et al, J. Biol. Chem. 264:2498–2501, 1989.
McLennan, G. et al, Radiat. Res. 84:122–132, 1980.
Jones J. B. et al, J. Otolaryngol., 19:299–306, 1990.
Kumar et al, Pharmac. Ther., 39:301, 1988.
Machlin L. J. and Bendich, F.A.S.E.B., 1:441–445, 1987.
Markland, S. et al, Oxy–Radicals and Their Scavenger Systems vol. II, Cellular and Medical Aspects, Greenwald, R. A., Cohen, G. eds. Elsevier Biomedical New York, 1982.
Twentyman, P. R., et al, JNCI, 64:595–603, 1980.
Brown, J. M. et al, JNCI, 64:605–611, 1980.
Bernstein, M. et al, Radiat. Res., 91:624–637, 1982.
Coleman, C. N., Seminars in Oncology, 16:169–75, 1989.
Petkau A, Molecular and Cellular Biochemistry, 84:133, 1988.
Breuer, Raphael et al., Lung 170: 19–29, 1992.
Malaker, K. and Das, R. M., Molecular and Cellular Biochemistry 84:141–145, 1988.
Malaker, K. and Das, R. M., Pharmac. Ther., 39:327–330, 1988.
Pollak et al., Strahlentherapie 154(7):499–502 (1978).
Leung et al., Cancer (Phila.) 71(7):2276–2285 (1993).
Allalunis–Turner et al., Int J Radiat Oncol Biol Phys 23(2):339–343 (1992).
Mashiba et al., Life Sci 49(19):1419–1426 (1991).
Skapek et al., Cancer Res 48(10):2764–2767 (1988).
Lespinasse et al., Radiat Res 110(1): 149–154 (1987).
Ono et al., Int J Radiat Oncol Biol Phys 12(9): 1661–1666 (1986).
Afanas'ev et al., Tr. Mosk. Obshchest. Ispyt. Prir. 32:15–18 (1970).
Kent et al., Radiat Res. 116(3):539–546 (1988).
Dinescu et al., Oncol. Radiol. 10(5):437–444 (1971).
Slaga et al., Cancer Research 37:1631–1635 Jun. 1977.

*Primary Examiner*—Marian C. Knode
*Assistant Examiner*—Jean C. Witz
*Attorney, Agent, or Firm*—Bereskin & Parr

[57] ABSTRACT

A method of treating tumor cells comprising administering a therapeutically effective amount of an antioxidant. In accordance with one aspect of the invention a method of treating tumor cells is provided comprising administering an antioxidant in an amount effective for sensitizing the cells to radiation or to a chemotherapeutic agent. Preferably, the method is used to radiosensitive tumor cells during radiotherapy in a mammal.

7 Claims, 1 Drawing Sheet

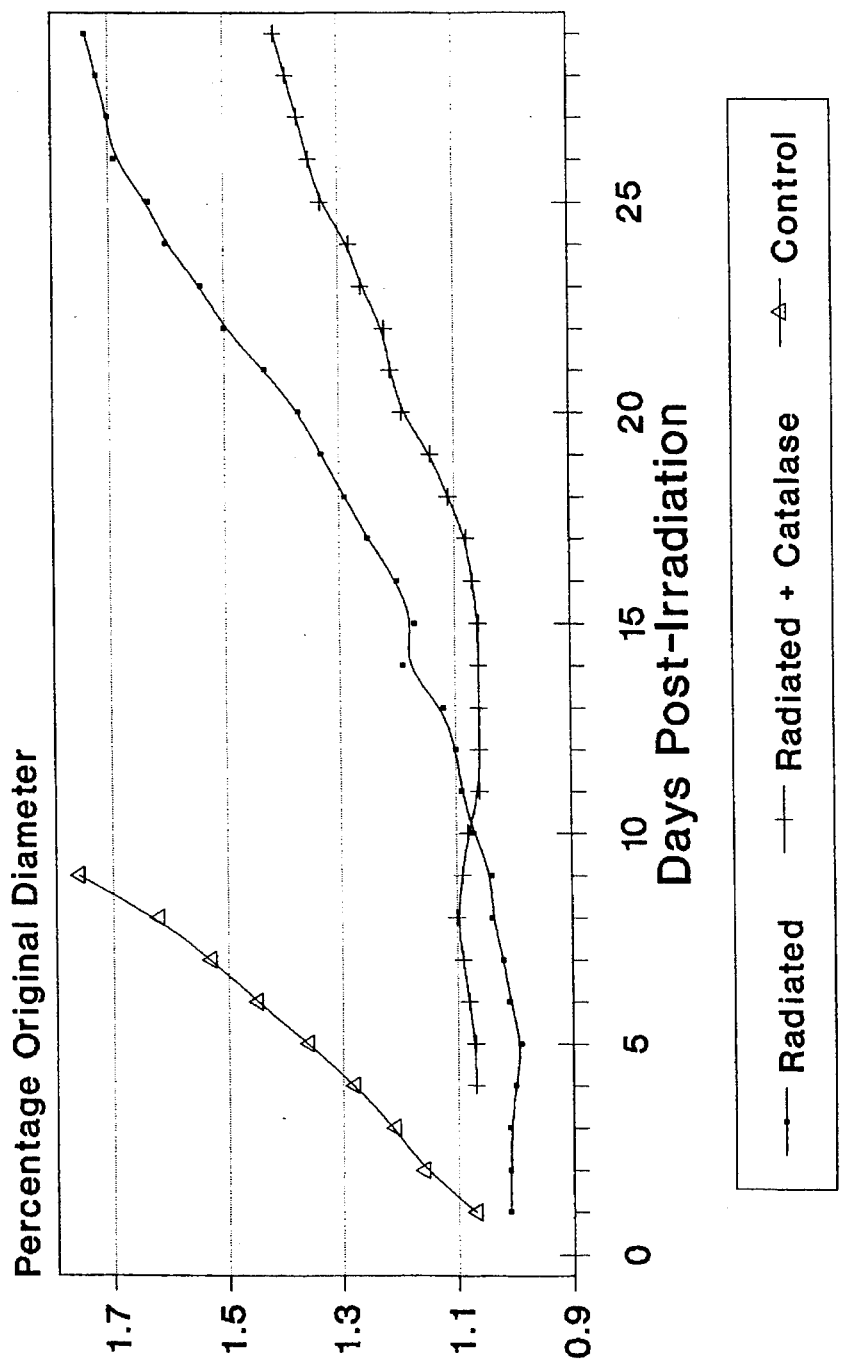

METHOD OF TREATING TUMOUR CELLS USING CATALASE

FIELD OF THE INVENTION

The present invention relates to the use of antioxidants to treat tumour cells; to pharmaceutical compositions containing antioxidants adapted for such use; and, to methods for the treatment of tumour cell by administering antioxidants.

BACKGROUND OF THE INVENTION

Ionizing radiation is a well established treatment modality for malignant disease and is of proven benefit for both curative and palliative purposes. The complications of radiotherapy are well known and include mucositis, leukopenia, desquamation, spinal cord necrosis, and obliterative endarteritis (Grosch, D. S., Hopwood, L. E., Biological Effects of Radiation, Academic Press, New York, San Francisco, 19791 Peters, L. J., Thawley, S. E., Panje, W. R., ed. Comprehensive Management to Head and Neck Tumours, W. B. Saunders Philadelphia, London, Toronto, 1987 pp. 13–152; Petkau, A., et al. Life Sci. 1978:22, 867–882). These complications frequently limit the ability to deliver a full therapeutic dose of radiation or cause significant morbidity following treatment. Thus, there has been an extensive search for agents which will either protect normal tissue from radio-injury without sparing the tumour, or will selectively sensitize malignant tissue to allow lower doses of radiation to achieve the same therapeutic effect with less damage to healthy tissues (Hall, E. J. Radiobiology for the Radiobiologist, 2nd edition, Harper and Row, Hagerstown, N.Y. 1978, Coleman, C. N., Seminars in Oncology, 16:3 169–75, 1989).

Ionizing radiation acts by displacing an electron from the outer shell of a molecule or atom, resulting in a species that is electron deficient (Grosch, D. S. Hopwood, L. E., Biological Effects of Radiation, Academic Press, New York, San Francisco, 1979; Clark I. A., Pathology, 1986:18,181–186; Thomas, J. K. Silini, G. ed. Radiation Research 1966:179–194; Southorn, P. A., Mayo Clin Proc. 63:381–389 (1988)). These electron deficient species are known as free radicals and are extremely unstable, reacting rapidly with adjacent molecules and atoms, causing alteration in their chemical structure (Grosch, D. S. Hopwood, L. E., Biological Effects of Radiation, Academic Press, New York, San Francisco, 1979; Clark I. A., Pathology, 1986: 18, 181–186; Thomas, J. K. Silini, G. ed. Radiation Research 1966: 179–194; Southorn, P. A., Mayo Clin Proc. 63: 381–389 (1988)). This chemical injury mediated upon DNA, particularly injury resulting in double strand DNA breaks, is responsible for tumour cell death in clinical radiotherapy (Grosch, D. S., Hopwood, L. E., Academic Press, New York, San Francisco, 1979; Peters, L. J., Thawley, S. E., Panje, W. R., ed. Comprehensive Management of Head and Neck Tumours, W. B. Saunders Philadelphia, London, Toronto, 1987 pp. 132–152, Clark, I. A., Pathology, 1986:18, 181–186; Hall, E. J. Radiobiology for the Radiobiologist, 2nd edition, Harper and Row Hagerstown, New York, 1978; Southorn, P. A., Mayo Clin. Proc. 63: 381–389 (1988)).

Radiolysis of the water molecule produces a free electron ($e^-$), a hydrogen ion ($H^+$), and the hydroxyl radical (OH)—a potent oxidizing agent (Grosch, D. S., Hopwood, L. E., Biological Effects of Radiation, Academic Press, New York, San Francisco, 1979; Thomas, J. K., Silini, G. ed. Radiation Research 1966: 179–194; Southorn, P. A., Mayo clin, Proc. 63: 381–389 (1988); Grezlinska, E. et al, Int. J. Radial. Biol. 1982:41, 473–481; McLennan G., Autor, A. P., Autor, A. P. ed. Pathology of Oxygen, Academic Press, New York, 1982, pp. 85–97; Petkau, A., Br. J. Cancer 55:Suppl VIII, 7–95 (1987)). The free electron can then be bound by other molecules to form additional unstable radicals (Grosch, D. S., Hopwood, L. E., Biological Effects Of Radiation, Academic Press, New York, San Francisco, 1979; Clark I. A., Pathology, 1986: 18,181–186; Southorn, P. A., Mayo clin, Proc. 63: 381–389 (1988); Grezlinska, E. et al, Int. J. Radiat. Biol. 1982:41, 473–481; Petkau, A., Br. J. Cancer 55:Suppl VIII, 87–95 (1987)). The most important of these is the reaction with molecular oxygen to form the superoxide radical ($O_2^-$) (Grosch, D. S., Hopwood, L. E., Biological Effects of Radiation, Academic Press, New York, San Francisco, 1979; Hall, E. J. Radiobiology for the Radiobiologist, 2nd edition, Harper and Row, Hagerstown, New York 1978, Coleman, C. N., Seminars in Oncology, 16:3 169–75, 1989); Clark I. A., Pathology, 1986:18,181–186; Grezlinska, E. et al, Int. J. Radiat. Biol. 1982:41, 473–481; McLennan G., Autor, A. P., Autor, A. P. ed. Pathology of Oxygen, Academic Press, New York, 1982, pp. 85–97; Petkau, A., Br. J. Cancer 55:Suppl VIII, 87–95 (1987)). These two radicals are responsible for most of the DNA injury mediated by radiotherapy. They do not discriminate, however, and damage to non-DNA structures, particularly the peroxidation of lipid membranes, cause many of the acute side effects of radiation without contributing to tumour cell death (Grosch, D. S., Hopwood, L. E., Biological Effects of Radiation, Academic Press, New York, San Francisco, 1979; Southorn, P. A., Mayo clin, Proc. 63:381–389 (1988); Grezlinska, E. et al, Int. J. Radiat. Biol. 1982:41, 473–481; Petkau, A., Br. J. Cancer 55:Suppl VIII, 87–95 (1987); Peters, L. J., Thawley, S. E., Panic, W. R. ed. Comprehensive Management of Head and Neck Tumours, W. B. Saunders Philadelphia, London, Toronto, 1987, pp. 132–152; Misra, H. P. and Fridovich, I., Arch Bioch Biophs 1986:176, 577–581).

The presence of dissolved oxygen significantly increases free radical generation and thus the effectiveness of radiation injury—the so-called oxygen effect (Grosch, D. S., Hopwood, L. E., Biological Effects of Radiation, Academic Press, New York, San Francisco, 1979; Hall, E. J. Radiobiology or the Radiobiologist, 2nd edition, Harper and Row, Hagerstown, New York 1978, Coleman, C. N., Seminars in Oncology, 16:3 169–75, 1989). The resistance of hypoxic tumours to radiation injury is well recognized in clinical practice and is a reflection of this effect.

A variety of radiosensitizers have been developed and studied. The majority of these are nitroimidazole compounds such as metronidazole, misonidazole, and etanidazole (Hall, E. J. Radiobiology for the Radiobiologist, 2nd edition, Harper and Row, Hagerstown, New York 1978, Coleman, C. N., Seminars in Oncology, 16:3 169–75, 1989; Schor, N. F., Biochem pharmacol 1988:37(9), 1751–1762). Peripheral neuropathy has been a significant complication from these agents and they have not developed into clinically useful agents (Hall, E. J. Radiobiology for the Radiobiologist, 2nd edition, Harper and Row, Hagerstown, New York 1978; Coleman, C. N., Seminars in Oncology, 16:3 169–75, 1989).

Radioprotection research has been directed mainly at free radical scavenging compounds based on the sulfhydryl (—SH) group (Hall, S. J. Radiobiology for the Radiobiologist, 2nd edition, Harper and Row, Hagerstown, New York 1978). Although early studies suggested these agents would provide relative protection of normal tissue compared to tumours, they also have not been shown to be clinically useful (Hall, E. J. Radiobiology for the Radiobiologist, 2nd edition, Harper and Row, Hagerstown, New York 1978; Coleman, C. N., Seminars in Oncology, 16:3 169–75, 1989). A major problem has been the necessity to preload the patient with these compounds to obtain adequate tissue levels given that most of these agents are metabolized and rendered inert by the liver (Hall, E. J. Radiobiology for the Radiobiologist, 2nd edition, Harper and Row, Hagerstown, New York 1978).

Superoxide dismutase (SOD) and catalase (CAT) are two intracellular enzymes which function to convert superoxide ($O_2^-$) to peroxide (HO:OH—essentially two hydroxyl radicals) and peroxide to water (Southorn, P. A., Mayo Clin. Proc. 63:381–389 (1988); Petkau, A., Br. J. Cancer 55:Suppl VIII, 87–95 (1987); Fridovich, I., Autor, A. P. ed pathology of Oxygen Academic Press, New York, 1982, pp. 1–20; McCord, J. M., J Free Radic Biol Med 1986:2, 307–310; McCord J. M., Science 1974:185, 529–531) previous studies have shown that SOD exerts a protective effect against free radical mediated injury from a variety of sources, including radiation (Clark I. A., Pathology, 1986:18,181–186; McLennan, G., Autor, A. P. ed Pathology of Oxygen, Academic Press, New York, 1982, pp. 85–97; McCord, J. M., J Free Radic Biol Med, 1986; 2, 307–310; McCord, J. M. et al, Autor, A. P. ed Pathology of Oxygen Academic Press, New York, 1982, pp.75–83Petrone, W. F. et al, Proc Natl Acad Sci USA, 1980:77, 1159–1163; Autor, A. P. Life Science, 1974:14, 1309–1319; McCord, J. M., Fed Proc, 1987:46, 2402–2406; Koyama, J. et al, Transplantation, 1985:40, 590–595; Atalla, SI. et al, Transplantation, 1985:40, 584–590; Manson, P. N. et al, Ann Surg 1983:198, 87–90;Petkau, A. et al, Biochem Biophys Res Commun, 1975:67, 1167–1174; Edsmyr, F., Autor, A. P. ed Pathology of Oxygen, Academic Press, New York, 1982, pp.315–326) although this has not been consistently found by all researchers (Westman, N. G. and Marklund, S. L., Acta Oncologica 1987:26, 483–487; Scott, M. D. et al, J. Biol. Chem. 1989:264(5), 2498–2501). CAT has been shown to provide a radioprotective effect in cell suspensions (Misra, H. P. and Fridovich, I., Arch Bioch Biophys, 1976:176, 577–581; McLennan, G. et al, Radial Res 1980:84, 122–132), and—more recently—in an in-vivo model (Jones J. B. et al, J Otolaryngol, 1990:19, 299–306).

Jones et al (Jones J. B. et al, J Otolaryngol, 1990:19, 299–306) studied the effect of SOD and CAT on radiation injury to rat skin. CAT was found to markedly ameliorate the acute radiation changes to rat epidermis and dermal vascular endothelium. SOD was found to have no protective effect by itself. The combination of SOD and CAT provided radioprotection similar to CAT alone—the addition of SOD had no additional beneficial effect.

SUMMARY OF THE INVENTION

Broadly stated the present invention relates to a method of treating tumour cells comprising administering a therapeutically effective amount of an antioxidant.

The invention also relates to a method of treating tumour cells comprising administering an antioxidant in an amount effective for sensitizing the cells to radiation or to a chemotherapeutic agent.

In a preferred embodiment of the invention a method is provided for radiosensitizing tumour cells during radiotherapy in a mammal which comprises administering to the mammal an amount of an antioxidant effective for sensitizing the cells to the radiotherapy.

The invention further relates to a pharmaceutical composition for treating tumour cells comprising a therapeutically effective amount of an antioxidant and at least one pharmaceutically acceptable carrier, diluent or excipient.

The invention still further relates to a pharmaceutical composition for sensitizing tumour cells to radiation or to a chemotherapeutic agent comprising an amount of an antioxidant effective to sensitize tumour cells to radiation or to a chemotherapeutic agent and at least one pharmaceutically acceptable carrier, diluent or excipient.

In a preferred embodiment of the invention a pharmaceutical composition for radiosensitizing tumour cells is provided comprising an amount of an antioxidant effective to sensitive the cells to radiation and at least one pharmaceutically acceptable carrier, diluent or excipient.

The present invention also contemplates the use of a therapeutically effective amount of an antioxidant enzyme to treat tumour cells, and use of an effective. amount of an antioxidant to sensitize tumour cells to radiation or to a chemotherapeutic agent.

BRIEF DESCRIPTION OF THE DRAWINGS

Further details of the invention are described below with the help of the examples illustrated in the accompanying drawings in which:

FIG. 1 is a graph showing tumour growth differential in a RIF fibrosarcoma model after treatment with radiation, radiation and CAT, and no treatment.

DETAILED DESCRIPTION OF THE INVENTION

The present inventors have determined that antioxidants increase the sensitivity of tumour cells to radiation in radiotherapy. In particular, the present inventors studied the effect of catalase on tumour tissue in a tumour model study using RIF-1 mouse fibrosarcoma tumour. Catalase was not found to protect these fibrosarcomas from radiation injury, confirming its potential safe use in radiotherapy. Unexpectedly, catalase was found to potentiate the injury the tumours suffered when exposed to radiation. The discovery of an agent which protects normal cells from radiation injury (radioprotector) while increasing the radiation-induced killing of tumour cells (radiosensitizer) is without precedent in the oncologic literature.

The present inventors findings also suggest that antioxidants such as CAT may be useful in the treatment of tumour cells and for enhancing or potentiating tumour injury by chemotherapeutic agents. Furthermore, the findings suggest that antioxidants such as CAT will be useful in treating cells and tissues after radiation damage.

Accordingly, as hereinbefore mentioned the present invention provides a method of treating tumour cells comprising administering a therapeutically selective amount of an antioxidant. In accordance with one aspect of the invention a method of treating tumour cells is provided comprising administering an antioxidant in an amount effective for sensitizing the cells to radiation or to a chemotherapeutic agent. Preferably, the method is used to radiosensitive tumour cells during radiotherapy in a mammal.

The term "antioxidant" used herein refers to agents that can remove free radicals from living cells and tissues. Antioxidants that may be utilized in the present invention are nutrients that can directly scavenge free radicals including Vitamin A, Vitamin E, tocopherol, Vitamin C (ascorbic acid), and beta-carotene; enzymes which catalyze the destruction of free radicals including peroxidases such as glutathione peroxidase (GSHPx) which acts on $H_2O_2$ and organic peroxides, catalase (CAT) which acts on $H_2O_2$, superoxide dismutase (SOD) which disproportionates $O_2$ to $H_2O_2$; glutathione transferase (GSHTx), glutathione reductase (GR), glucose 6-phosphate dehydrogenase (G6PD), and mimetics, analogs and polymers thereof; glutathione; ceruloplasmin; cysteine, and cysteamine (beta-mercaptoethylamine). A review of antioxidant enzymes and mimetics thereof and antioxidant nutrients can be found in Kumar et al, Pharmac. Ther. Vol 39: 301, 1988 and Machlin L. J. and Bendich, F.A.S.E.B. Journal Vol.1:441–445, 1987 which are incorporated herein by reference. Examples of analogs and polymers of antioxidant enzymes, such as SOD, are those described in U.S. Patent Serial No. 5,171,680 which is incorporated herein by reference.

Preferably, antioxidant enzymes are utilized in the methods of the invention, most preferably peroxidases. The antioxidant enzymes may be obtained from various mammalian species, preferably humans.

Catalase (CAT) has a number of properties which make it particularly advantageous to use in the present invention. CAT is a naturally occurring enzyme found in the intracellular fluid. It is occasionally released into the extracellular fluid when cell breakdown occurs and it has not been associated with any adverse effects. CAT has a short plasma half-life of 4 minutes (McLennan G., Autor, A. P. ed Pathology of Oxygen, Academic Press, New York 1982, pp. 85–97; McCord, J. M., J Free Radic. Biol. Med. 1986:2, 307–310), undergoing rapid renal clearance. Therefore, CAT would be active only for the duration of the radiation exposure and would not accumulate in the body, or be present for a long period of time for immunologic processing and reaction. CAT could also be given at the time of radiotherapy and no preloading would be required. CAT does not cross cell membranes (Markland, S. et al, Oxy-Radicals and Their Scavenger Systems Volume II, Cellular and Medical Aspects, Greenwald, R. A., Cohen, G. eds. Elsevier Biomedical New York, 1982). When administered intravenously CAT remains in the ECF (Markland, S. et al, Oxy-Radicals and Their Scavenger Systems Volume II, Cellular and Medical Aspects, Greenwald, R. A., Cohen, G. eds. Elsevier Biomedical New York, 1982). Intracellular free radicals generated by radiotherapy would not be scavenged and DNA damage should not be affected.

The administration of an antioxidant increases the sensitivity of tumour cells to radiotherapy and is expected to have a chemotherapeutic effect and potentiate or enhance the damage to tumour cells by chemotherapeutic agents. Thus, antioxidants may be used for the treatment of various forms of malignant diseases such as leukemias, lymphomas (Hodgkins and non-Hodgkins), plasmacytomas, histiocytomas, melanomas, adenomas, sarcomas, carcinomas of solid tissues, hypoxic tumours, squamous cell carcinomas of the mouth, throat, larynx, and lung, geninourinary cancers such as cervical and bladder cancer hematopoietic cancers, head and neck cancers, and nervous system cancers. Treatment with antioxidants may also allow for more effective radiotherapy of tumours that currently respond poorly to radiotherapy such as adenocarcinomas of the bowel and lung. Preferably antioxidants are used to treat radiosensitive malignancies such as melanomas, head and neck cancers, lung cancers, genitourinary cancers, lymphomas, hematopoietic cancers and nervous system cancers.

The antioxidants may be administered to treat malignant diseases in mammals, preferably humans.

In one aspect of the invention an antioxidant may be used to treat tumour cells or to potentiate or enhance the injury to tumour cells by chemotherapeutic agents. When the antioxidant is used to potentiate or enhance the injury to tumour cells by chemotherapeutic agents the antioxidant is generally administered prior to or simultaneously with administration of the chemotherapeutic agent. Chemotherapeutic agents which are expected to be potentiated or enhanced by the antioxidant enzymes include alkylating agents and agents which block the cells ability to regenerate DNA. Examples of chemotherapeutic agents that may be used in the present invention are melphalan, cyclophosphamide, CCNU i.e. 1-(2-chloroethyl)-3-cyclohexyl-1-nitrosurca, chlorambucil, doxorubicin, fluorouracil, carmustine, bleomycin sulfate, daunorubicin, cisplatin, cytarabine, dacarbazine, mitomycin, mitoxantrone hydrochloride, etoposide and streptozocin.

The antioxidant may be incorporated into a pharmaceutical composition to treat tumour cells either alone or together with other active substances including chemotherapeutic agents. Such pharmaceutical compositions can be for oral, topical, rectal, parenteral, local, inhalant or intracerebral use. They are therefore in solid or semisolid form, for example pills, tablets, creams, gelatin capsules, capsules, suppositories, soft gelatin capsules, gels, membranes, tubelets. For parenteral and intracerebral uses, those forms for intramuscular or subcutaneous administration can be used, or forms for infusion or intravenous or intracerebral injection can be used, and can therefore be prepared as solutions of the active compounds or as powders of the active compounds to be mixed with one or more pharmaceutically acceptable excipients or diluents, suitable for the aforesaid uses and with an osmolarity which is compatible with the physiological fluids. For local use, those preparations in the form of creams or ointments for topical use or in the form of sprays should be considered; for inhalant uses, preparations in the form of sprays, for example nose sprays, should be considered. Dosages to be administered depend on individual needs, on the desired effect and on the chosen route of administration, but daily dosages to humans by subcutaneous, intramuscular or intracerebral injection generally vary between about 0.001 and 1000 mg of active substance per Kg body weight, preferably between 1.0 and to 500 mg per Kg body weight. If the active substance is catalase the dosage may be from about 10 to $10^7$ units of catalase activity per kg of body weight.

The pharmaceutical compositions of the invention can be prepared by per se known methods for the preparation of pharmaceutically acceptable compositions which can be administered to patients, and such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985).

On this basis, the pharmaceutical compositions include, albeit not exclusively, solutions of the antioxidants in association with one or more pharmaceutically acceptable vehicles or diluents, and contained in buffered solutions with a suitable pH and iso-osmotic with the physiological fluids.

When employed as a radiosensitizer, the antioxidant is administered to a patient preferably having radiation sensitive tumour cells, prior to, simultaneously with, or after irradiation of the tumour cells. Preferably, the antioxidant is administered just prior to radiotherapy so that there are adequate tissue levels of the antioxidant while radiation is administered.

The antioxidants may be administered by any means that effect the radiosensitization of tumour cells in patients undergoing radiotherapy. For example, administration can be parenterally, subcutaneously, intravenously, intramuscularly or intraperitoneally. Alternatively or concurrently, administration can be by the oral route. Preferably, administration is parenteral. The dosage administered will be dependent upon the age, health, and weight of the recipient, kind of concurrent treatment, if any frequency of treatment, and the nature of the effect desired. Generally, the dosage of active ingredient compounds may be from about 0.001 to 1000 mg per kg of body weight. Preferably, from 1 to 500 mg per kg body weight per application, in one or more applications per radiotherapy may be used to obtain a desired result. If the radiosensitizer is catalase the dosage may be from about 10 to $10^7$ units of catalase activity per kg of body weight.

It will be appreciated that the particular radiation dose to be utilized in treating tumours will depend on a variety of factors, which factors are independent of the presence or absence of the antioxidant. Thus, the dosages of radiation, preferably X-rays, used in the present invention are fixed by the particular requirements of each situation. The dosage will depend on the size of the tumour, the location of the tumour, the age and sex of the patient, the frequency of the dosage, the presence of other tumours, possible metastases and the like. The presence of the antioxidant increases the number of tumour cells that are killed by radiation. The pre-set dosage radiation therefore is expected to become more effective in the presence of the antioxidants than in their absence. Those skilled in the art of radiotherapy can readily ascertain the dosage for any particular tumour by reference to the following textbooks Hall, E. J. Radiobiology for the Radiobiologist, 2nd edition, Harper and Row Hagerstown, New York, 1978 and Biological Effects of Radiation, Academic Press, New York, San Francisco, 1979; Peters, L.J., Thawley, S. E., Panje, W. R., ed. W. B. Saunders Philadelphia, London, Toronto, 1987 which are incorporated herein by reference.

The antioxidants when used as radiosensitizers can be employed in dosage forms such as tablets, capsules powder packets or liquid solutions, suspensions or elixirs for oral administration, or sterile liquids for formulations such as solutions or suspensions for parenteral use. In such pharmaceutical compositions, the active ingredient will be present in an amount of at least 0.5% by weight based upon the total weight of the composition and not more than 90% by weight. A pharmaceutically acceptable carrier, diluent or excipient as described in detail above is preferably used in the compositions.

The following non-limiting example is illustrative of the present invention:

EXAMPLE 1

This example describes a study investigating the effect of catalase on radiotherapy of malignant tumours. The study uses a model which is well established and has been used in studies related to radiation effects on tumour tissue (Twentyman, P. R., et al, JNCI 1980:64, No.3, 595–603; Brown, J. M. et al, JNCI 1980:64, No. 3, 603–611; Bernstein, M, et al, Radiat Res, 1982:91, 624–637).

The following materials and methods were used in the study illustrated in the example:
RIF-1 Tumour Model The RIF-1 tumour is well suited to studies of radiation response, including in vitro cell survival and in vivo tumour studies. It is a rapidly growing tumour with a doubling time of 65 hours and a cell cycle time of 12 hours (Twentyman, P. R., et al, JNCI 1980:64, No.3, 595–603; Brown, J. M. et al, JNCI 1980:64, No. 3, 603–611; Bernstein, M, et al, Radiat Res, 1982:91, 624–637). The RIF-1 tumour is minimally immunogenic, and metastasizes only at a late stage of growth.

Tumours were produced by the subcutaneous inoculation into the lower backs of mice. This inoculation consisted of a suspension of $2\times10^5$ RIF-1 cells from culture in 0.25 ml of alpha minimum essential media[a] (MEM, Gibso), supplemented with 10% fetal bovine serum[b] (Johns Scientific). Male C3H/He mice[c] (Harlan Sprague Dawley Inc., Indianapolis, Ind.), 5 to 7 weeks old at the time of inoculation, were used for all experiments. Animals were anaesthetized by inhalation of methoxyflurane[d] (metofane, Pitman-Moore Ltd.) for the inoculation.

The tumours were then allowed to grow to 1 cm in average diameter. Measurements were made using a calliper, taking the tumour length and width and calculating the average of these two. Tumour diameter measurements were taken every 2 to 3 days from the time the tumour cells were implanted.
Therapeutic Protocol The animals were housed two to a cage, fed a standard pelleted diet, and allowed free access to water. Tumours were allowed to grow to approximately 1 cm average diameter without any intervention.

At the time that the tumours reached 1 cm average diameter, the subject animal was randomized into one of three groups. Group One (19 mice) received no radiation and no enzyme, Group Two received radiation and no enzyme, and Group Three received radiation and enzyme.

All animals received a general anaesthetic using intraperitoneal ketamine and xylasine. All animals were immobilized in a specially designed chuck and placed in the radiotherapy apparatus for the same period of time, and those in Group One were sham irradiated. No animal was noted to have moved or aroused from the state of general anaesthesia by the end of any of the radiotherapy sessions. The radiation exposure consisted of a single dose of 3000 cGy of 150 KeV X-irradiation (mean time 10 minutes, 40 seconds), and the radiotherapy equipment was calibrated (Protea ionization chamber) before and after each session to ensure absolute uniform dosing. The radiotherapy was administered with a cone over the tumour and lower back of the animal, which in every case assured a uniform maximal delivery dose to the tumour while minimizing dose delivery to the sensitive structures of the abdomen and upper pelvis.

Those animals randomized to the enzyme-treated group received an intravenous dose of 10,000 units/kg body weight CAT (SIGMA chemical Corp., St. Louis). All enzymes were injected via the dorsal penile vein immediately (within 30–60 seconds) prior to commencing irradiation. Usually, the tail vein is the principle injection site in this animal. However, when starting the experiment the injection of sterile water was attempted under sterile conditions while several animals were under anaesthesia for the purposes of tumour cell inoculation and it could not be ensured that intravenous injection was achieved in these cases. During injection through the easily accessible dorsal penile vein, intravenous injection could be seen as it occurred and was therefore considered a more reliable method of enzyme administration.
Post-Treatment Protocol All animals remained under examination until complete recovery from general anaesthesia had occurred, at which point they were returned to the vivarium. All animals were marked with ear punches and placed in numbered cages in a random fashion, again with two animals per cage. Records regarding the animal's experimental status were sealed, and all subsequent measurements were made by blinded observers and recorded according to the animal's number.

The day the subject animal was treated was designated Day Zero. At frequent intervals, usually every other day, the tumours were measured in the same fashion as previously described, and an average of two diameters calculated. These data were plotted as a function of time.

The end-point of the study occurred when the tumour reached double the original treatment diameter, or approximately 2 cm. Animals were euthanized in a $CO_2$ chamber and the tumours removed surgically post-mortem. Tumours were then placed in formalin and stored in the event that further study would be needed. Two representative tumours were sectioned, paraffin embedded and slides were stained using H&E stain and examined by a pathologist to confirm the histological presence of RIP-1 fibrosarcoma.

Criteria for premature sacrifice and/or tumour harvesting, before the tumour reached twice the original treatment diameter, were assigned (1) Premature death of animal following Day Zero
(2) Ulceration of the tumour
(3) Infection/inflammation of the injection site Data Retrieval and Statistical Analysis Following the termination of the experiment, growth curves for each subject tumour were completed and a line of best fit assigned for purposes of interpolation between data points. The average diameter (AD) of each tumour was then determined for each day of the study from the lane of best fit. For reasons of uniformity of analysis between subjects and because of the slight variation in average measurements on Day Zero, each day's AD measurement was calculated as a percentage of the AD of the tumour on Day Zero and charted (i.e. AD Day Zero=0.9 cm, AD Day Ten=1.2; therefore AD Day Ten=1.3 AD Day Zero). Data obtained in this fashion was then unlocked from the scaled key and the tumours were sorted into the appropriate experimental group.

Subsequently, the data for each of Groups One, Two and Three of subject animals was analyzed for each day following Day Zero. The mean AD, standard deviation and number of animals available for each post-therapy day was calculated statistically. This information was then charted in line graph form (FIG. 2) and the information gleaned subjected to a rigorous statistical analysis.

Results

The results of the study are as follows. No complications occurred due to the tumour cell inoculation process or the associated general anaesthesia. Sixty-two male C3h/He mice were used, and sixty-two tumours were obtained. One animal did not grow a tumour and one animal grew two tumours which were satisfactory to be measured separately. No complications occurred due to tumour growth before the tumours reached an AD of approximately 1 cm.

Due to the rapid growth of this tumour, it was impossible to treat every tumour at an AD of precisely 1 cm. The mean AD of the whole group of 62 tumours on Day Zero ($AD^0$) was 1.07 cm (standard deviation=0.16 cm) and did not vary statistically between the three experimental groups. The mean time taken for the tumours to reach this $AD^0$ was 34 days post-inoculation (standard deviation=16 days) and this did not vary statistically between groups.

As a result of the randomization, Group One, the group which received no radiation and no enzyme (CONTROL), contained 19 animals. Group Two, which received radiation and no enzyme (RT), contained 22 animals; and Group Three, which received radiation and enzyme (RT+CAT), contained 21 animals.

No complications occurred on Day Zero, either as a result of the general anaesthetic, the injection of sterile water or catalase, or the radiotherapy session. All animals appeared to tolerate the procedure well and recovered well in the immediate post-therapy period.

43 tumours were followed and serially measured to the planned experimental endpoint of double the $AD^0$ ($2 \times AD^0$). 19 animals were sacrificed prior to the planned endpoint due to the following complications:

(1) premature death of animal following $AD^0$ and prior to growth to $2 \times AD^0$ Total animals lost 3

| Control group | 0/19 animals |
| --- | --- |
| (RT) group | 1/22 animals on Day 5 |
| (RT + CAT) group | 2/21 animals on Days 12, 25 |

Limited autopsies of the involved mice ruled out macroscopic metastatic decease and was unsuccessful in determining the etiology of the causes of death. Statistical analysis of this data was carried out using the Fisher's exact test to determine if the differences seen between groups was significant. The differences seen between groups was not significant (p=0.607), suggesting that the deaths seen in the (RT+CAT) group cannot be attributed to catalase. Also, the time at which the deaths occurred, 5 to 25 days post-therapy, suggest that they were likely due to tumour effects or the general health of the animals, and not the effect of the radiotherapy or the enzyme treatment.

(2) Ulceration of the tumour

Total animals lost 3

| Control group | 0/19 animals |
| --- | --- |
| (RT) group | 5/22 animals |
| (RT + CAT) group | 8/21 animals |

Statistical analysis of this data was carried out using the Fisher's exact test to determine if the differences seen between groups was significant. The differences seen between the control group and the two radiated groups were significant (p=0.0036). However, the difference in the incidence of ulcers between the (RT) and (RT+CAT) groups was not significant (p=0.332). This suggests that the tumour necrosis which results in ulceration of the surface of the tumour is the result of the radiotherapy, which is in keeping with the tumour-cell killing activity of radiation. These findings also suggest that the extra ulcers seen in the (RT+CAT) group cannot be attributed to catalase treatment.

(3) Infection/inflammation of the injection site

Total animals lost 3

All from the (RT+CAT) group

The (RT+CAT) group was the only group receiving intravenous injection on Day Zero. It should be noted that no such injection site complications were observed in two previous studies (Edsmyr, F., Autor, A. P. ed Pathology of Oxygen, Academic Press, New York, 1982, pp. 315–326; Westman, N. G., et al, Acta Oncologica 1987:26, 483–487) injecting catalase into the dorsal penile veins of Wistar rats. This suggests that the choice of injection site other than the recommended primary injection site for the mouse was responsible for the small number of injection site infections that were observed.

For reasons of uniformity of analysis between subjects and because of the slight variation in average measurements on Day Zero each day's AD measurement was calculated as a percentage of the AD of the tumour on Day Zero and charted. For purposes of discussion, the resulting value is referred to as the "Relative Average Diameter" or RAD, followed by the post-therapy day number as a superscript (i.e. AD Day Zero=0.9 cm, AD Day Ten=1.2; therefore AD Day Ten=1.3 AD Day Zero; therefore $RAD^{10}$=1.3). This method has the advantage of relating all tumour size changes within a group to each other, regardless of slight differences in the starting size.

The resulting data was then analyzed in three distinct ways as described below to determine if there were statistically significant differences between the three groups.

(1) Volume doubling Time (VDT)

The time taken for the tumour to double in volume was calculated using the AD and computing the volume of the tumour as for a sphere with the same average diameter (therefore, the target diameter was 1.25 $AD^0$ (spherical volume=$4/3 \times pi \times \{AD/2\}^3$)). The volume doubling time (VDT) was determined for each tumour and an analysis was carried out to calculate the mean, standard deviation, and n, the number of subjects per group that reached double the original volume (Table 1).

A student's t-test was performed on the resulting raw, untransformed data obtained for the VDT, and the same calculation was undertaken using transformed data (a logarithmic transformation of all raw values). All values found to be statistically significant in this analysis were subjected to further verification using the Wilcoxon adjustment and again with the Bonferoni adjustment. Finally, multiple comparison testing ("Tukey's Honestly Significant Difference Test") was done for each value quoted as significant. This was accomplished by establishing significance in each of the analyses of untransformed data (raw data), transformed data (fourth root conversion), and rank score (nonparametric analysis) before labelling a trend or statistical finding significant. For uniformity, p-values quoted are those obtained for the transformed data.

It should be noted that the RIF-1 control tumours were very fast growing, with a mean VDT of 3.5 days from 1 cm diameter, and this is in keeping with the growth rates described in the literature on RIF-1 (McLennan, G., et al, Radial Res 1980:84, 122–132; Jones, J. B. et al, J Otolaryngol, 1990:19, 299–306). The VDT value of the control group differed significantly from the other two groups, with the two radiated groups having significantly longer volume doubling times than the unradiated controls (Control vs. {RT}, p<0.001; Control vs. {R+CAT}, p<0.001). This is in keeping with the expected theory that tumour cells are killed in radiotherapy, and the smaller number of cells left take a longer time to replenish and redouble (Hall, E. J., Radiobiology for the Radiobiologist, 2nd edition, Harper and Row, Hagerstown, New York 1978). Also, the fact that there was a significant difference noted between the Control vs. {RT+CAT} group indicates that tumours in the enzyme-treated group did not behave biologically like unradiated tumours. This therefore supports the hypothesis that catalase does not protect tumours from radiation injury.

An unexpected finding obtained from these data is that the VDT value of the {RT+CAT} group is actually greater than the VDT of the {RT} group. This finding was subjected to the same statistical analysis and is significant (p<0.001). This indicates that the tumours in the enzyme-treated group regrow and redouble slower than the purely radiated tumours, indicating greater tumour injury results from radiotherapy and catalase together (Hall, E. J., Radiobiology for the Radiobiologist, 2nd edition, Harper and Row, Hagerstown, New York 1978; Twentyman, P. R., et al, JNCI 1980:64, No. 3, 595–603).

(2) Growth Curves

The data for each of Groups One, Two and Three of subject animals was analyzed for each day following Day Zero. The mean RAD, standard deviation and number of animals available for each post-therapy day was calculated statistically. This method has the advantage of including as many subject tumours as possible, regardless of premature loss of the animal before ($2 \times AD^0$). It should be noted that, as a result of this, the n for each data point charted decreased from Day Zero to the termination of the study period.

The information obtained in this fashion was then charted in line graph form for the first 30 days (FIG. 1).

As shown in FIG. 1, all three curves begin to converge after 30 days, and this is due to the fact that many animals had reached the target endpoint of the study ($2 \times AD^o$), were sacrificed and not allowed to continue to grow, thereby removing from the group the fastest growing tumours, retaining the slower growing tumours which had not reached the target endpoint and keeping the mean RAD under ($2 \times AD^o$) longer. Also, as the study period continued, more animals were lost due to the three complications outlined above, in some cases losing some of the larger tumours to necrosis and ulceration. It was therefore most appropriate to scrutinize the data for the first 30 days to avoid the above contamination of data.

It should be noted again that the unradiated control tumours had a very brisk growth pattern, following an exponential growth curve throughout the range of the study. It is also seen that the {RT} group tumours reached a plateau for a period of time after Day Zero and regrew in a delayed fashion, as suspected and proved in the above VDT analysis. Again, unexpectedly, the {RT+CAT} group was seen to plateau and regrow in a delayed fashion, more delayed than the {RT} group. This difference was maximal for the rad value 1.4, where it took the catalase-treated group 9 extra days to reach this RAD than the purely radiated group. This again suggests a greater tumour injury with the combined use of radiotherapy and catalase injection.

(3) Time-to-Event Analysis

The difference in the trends shown by the growth curves (FIG. 2) of the {RT} and {RT+CAT} groups was subjected to another form of statistical analysis, "time-to-event" analysis, to verify that these groups of tumours are behaving differently at multiple points in their post-therapy growth pattern.

Specifically, the time taken to reach 1.2, 1.4, 1.6, 1.8 and 2.0 RAD were plotted on "Time-to-Event" survival curves, Kaplan-Meier estimates calculated, and the appropriate p-values obtained.

Significant differences in the survival curves were found for RAD values of 1.2 (p=0.018) and 1.4 (p=0.009). Due to data contamination and the convergence of the curves above RAD 1.5, as mentioned above, significant differences were not found at 1.6 (p=0.114), 1.8 (p=0.425), or 2.0 (p=0.846). FIG. 1 shows the growth survival curve for RAD 1.4. This finding of multiple significant points of difference in "time-to-event" survival curves indicates different biological behaviour in the {RT} and {RT+CAT} groups of tumours post-therapy.

In summary, analysis of volume-doubling time, tumour diameter growth curves and "time-to-event" survival curves statistically confirms the finding of delayed tumour regrowth following treatment with radiation and catalase as compared to using catalase alone. This indicates that more tumour injury occurs in the enzyme-treated group on Day Zero. The magnitude of this statistically significantly increased tumour injury can be indirectly measured in this sub-lethal, noncurative tumour study (See Table 2) and has important ramifications for the use of free radical scavenging enzymes in the treatment of malignant disease.

Comparison of the time required for tumours treated with radiotherapy (RT) (group 2) and RT+CAT (group 3) to regrow and redouble shows that the tumours treated with CAT show no resistance to radiation, but in fact, an increased sensitivity to it.

In all cases, tumour in group 2 (RT alone) had a significantly higher VDT than untreated controls (group 1). Treatment with radiation, as expected, showed a significant tumouricidal effect on the RIP-1 tumour. It can be concluded that the radiation given in this experiment was effective in killing RIF-1 tumour cells.

Comparing the radiation group (group 2) to the R+CAT group (group 3) also showed significant differences. In all cases, tumours treated with catalase and radiation required significantly longer periods of time to double in volume, and to regrow to 1.2, 1.4 $AD^o$ when compared no those treated with radiation alone.

Radiation affects tumours by causing a fixed percentage kill of tumours cells per radiation dose (Hall, E. J. Radiobiology for the Radiobiologist, 2nd edition, Harper and Row, Hagerstown, New York, 1978). Remaining tumours cells, in the absence of further radiation, continue to multiply and repopulate the tumour mass resulting in increased tumour size over time (Hall, E. J. Radiobiology for the Radiobiologist, 2nd edition, Harper and Row, Hagerstown, New York, 1978). The greater the initial tumour cell kill, the longer it takes the tumour to regrow to its initial and eventually larger size.

This study shows that radiation in the presence of catalase results in a significantly higher initial tumour cell kill than radiation alone. It is expected that this may have important therapeutic implications.

Each dose of radiation kills a fixed fraction of tumour cells. Multiple dose fractionation as currently employed is designed to maximize tumour kill while keeping radiation side effects to a minimum (Peters, L. J., Thawley, S. E., Panje, W. R. ed. Comprehensive Management of Head and Neck Tumours, W. B. Saunders Philadelphia, London, Toronto, 1987, pp. 132–152). These side effects, however, are still a major source of morbidity and sometimes mortality. Increasing tumour sensitivity to ionizing radiation would allow or the same therapeutic goals to be reached with fewer doses of radiation and thus fewer side effects. Alternatively, current radiation dose schedules could be maintained with the expectation that greater tumour control could be achieved without an increase in morbidity. This may allow for effective radiation treatment for tumours that currently respond poorly to radiotherapy.

Catalase also presents several advantages over other radiosensitizing agents. Firstly, it is a normal constituent of the intracellular fluid. It does occur occasionally in the extracellular fluid when tissue damage (e.g. hemolysis) occurs but no adverse side effects have been attributed to this molecule. Also, side effects of catalase administration have not been described in the literature, nor have they been witnessed in previous experimental use by our group (Jones, J. B., et al, J Otolaryngol, 1990:19, 299–306).

Secondly, catalase can be administered at the time of radiotherapy. This would obviate the need for pre-administration to obtain adequate tissue levels as had been necessary with other agents. The short half-life and rapid clearance of catalase would also suggest minimal or no accumulation in the body.

Thirdly, catalase has also been shown to ameliorate the acute side effects of radiation in normal tissue. Thus, catalase appears to show some of the ideal characteristics of a pharmacological adjunct to radiotherapy—namely providing sensitization of tumour cells while also providing protection of normal tissue (Hall, E. J. Radiobiology for the Radiobiologist, 2nd edition, Harper and Row, Hagerstown, New York, 1978).

The reasons for the radiosensitizing effect of catalase may relate to its catalyzation of peroxide to water and $O_2$ in the extracellular fluid. This would conceivably have two effects. Firstly, there would be a reduction in ECF hydroxy radicals (OH.). This would allow for a reduced peroxidation of the lipid membrane. Secondly, there would be an increase in extracellular $pO_2$. Currently, radiolysis of extracellular $H_2O$ promotes consumption of ECF $O_2$ to produce superoxide as previously discussed. This ECF superoxide does not contribute tumour cell DNA damage. However, the production of ECF superoxide results in consumption of ECF $O_2$ and subsequently a drop in ECF $pO_2$. Thus, there is reduced oxygen in the ECF and, as ICF $pO_2$ is dependent on ECF $pO_2$, a concomitant reduction in intracellular oxygen.

By essentially increasing extracellular oxygen levels during radiation, catalase may also provide for elevated intracellular oxygen levels as oxygen diffuses passively across the cell membrane. This would then allow for increased intracellular free radical generation by radiation where critical cell structures, especially DNA, would be damaged. This may be confirmed by obtaining microelectrode $pO_2$ measurements.

It must also be considered that catalase exerts its tumouricidal effect completely independently radiation.

Catalase has not previously been shown to have a radiosensitizing effect. However, this study has shown a highly significant increase in RIF-1 tumour cell kill by radiation in the presence of catalase when compared to radiation alone.

The present invention has been described in detail and with particular reference to the preferred embodiments; however, it will be understood by one having ordinary skill in the art that changes can be made thereto without departing from the spirit and scope thereof.

TABLE 1

VOLUME DOUBLING TIME FOLLOWING DAY ZERO

| Group | n | Standard Deviation | Mean |
|---|---|---|---|
| Control Group One | 19 | 3.40 | 3.58 days |
| RT alone Group Two | 18 | 7.31 | 18.17 days |
| RT + Cat Group Three | 15 | 13.67 | 26.13 days |

TABLE 2

ROUGH CALCULATION OF ENHANCEMENT RATIO

Let the following symbols represent:

x     starting diameter Day Zero
$y^r$     number of tumor cellis killed in the {RT} tumor group
$y^c$     number of tumor cells killed in the {RT + CAT} group Calculation of $y^r$:

$2x/21 = 2.201 (x - y^r)/18$
$y^r = 0.221$

TABLE 2-continued

ROUGH CALCULATION OF ENHANCEMENT RATIO

Calculation of $y^c$:

$2x/29 = 2.201 (x - y^c)/18$
$y^c = 0.436$
Calculation of enhancement ratio (ER):

$ER = y^c/y^r$
$ER = 1.97$

We claim

1. A method of selectively radiosensitizing fibrosarcoma cells during radiotherapy in a mammal which comprises administering to a mammal having a radiation sensitive fibrosarcoma an antioxidant in an amount effective for selectively sensitizing the fibrosarcoma cells to radiation injury, wherein the antioxidant is catalase.

2. The method as claimed in claim 1 wherein the antioxidant is administered concurrently with the radiotherapy.

3. The method as claimed in claim 1 wherein an amount of catalase in a range of between 10 to $10^7$ units of catalase per kg of body weight of the mammal is administered.

4. A method of selectively radiosensitizing fibrosarcoma cells during radiotherapy in a mammal, which comprises administering to a mammal having a radiosensitive fibrosarcoma, an amount of catalase sufficient to selectively sensitize the fibrosarcoma cells to radiation injury, wherein the catalase is administered at substantially the same time as the radiotherapy.

5. The method as claimed in claim 4 wherein an amount of catalase in a range of between 10 to $10^7$ units of catalase per kg of body weight of the mammal is administered.

6. A method of selectively killing fibrosarcoma cells in a mammal having a radiation sensitive fibrosarcoma, comprising simultaneously administering to the mammal an antioxidant and a dose of radiation sufficient to selectively kill the fibrosarcoma cells without killing substantial numbers of normal cells, wherein the antioxidant is catalase.

7. The method as claimed in claim 6 wherein an amount of catalase in a range of between 10 to $10^7$ units of catalase per kg of body weight of the mammal is administered.

* * * * *